(12) United States Patent
DeLuca et al.

(10) Patent No.: US 7,259,143 B2
(45) Date of Patent: Aug. 21, 2007

(54) METHOD OF EXTENDING THE DOSE RANGE OF VITAMIN D COMPOUNDS

(75) Inventors: Hector F. DeLuca, Deerfield, WI (US); John W. Pike, Madison, WI (US); Nirupama Shevde, Madison, WI (US); Lori A. Plum, Madison, WI (US); Margaret Clagette-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 403 days.

(21) Appl. No.: 10/235,244

(22) Filed: Sep. 5, 2002

(65) Prior Publication Data
US 2004/0053813 A1 Mar. 18, 2004

(51) Int. Cl.
*A61K 38/00* (2006.01)
*A61K 31/59* (2006.01)

(52) U.S. Cl. ............................ 514/12; 514/2; 514/167

(58) Field of Classification Search ................ 514/2
See application file for complete search history.

(56) References Cited

U.S. PATENT DOCUMENTS

| | | | |
|---|---|---|---|
| 5,391,567 A * | 2/1995 | Raisz et al. ................ 514/443 |
| 5,780,437 A * | 7/1998 | Goulet et al. ................ 514/19 |
| 5,843,678 A | 12/1998 | Boyle ........................ 435/7.1 |
| 5,843,928 A * | 12/1998 | Deluca et al. ............... 514/167 |
| 6,015,938 A | 1/2000 | Boyle et al. .................. 800/18 |
| 6,034,075 A * | 3/2000 | Thys-Jacobs ............... 514/168 |
| 6,087,555 A | 7/2000 | Dunstan et al. .............. 800/18 |
| 6,271,349 B1 | 8/2001 | Dougall et al. ............. 530/351 |
| 6,284,485 B1 | 9/2001 | Boyle et al. ................ 435/69.1 |
| 6,284,740 B1 | 9/2001 | Boyle et al. .................. 514/44 |
| 6,288,032 B1 | 9/2001 | Boyle et al. .................. 514/12 |
| 6,316,408 B1 | 11/2001 | Boyle ........................ 514/12 |
| 6,335,170 B1 | 1/2002 | Orntoft .......................... 435/6 |
| 6,369,027 B1 | 4/2002 | Boyle et al. .................... 514/2 |
| 6,489,288 B1 * | 12/2002 | Lunenfeld .................... 512/15 |
| 6,503,893 B2 * | 1/2003 | Bishop et al. .............. 514/167 |
| 2003/0158154 A1 * | 8/2003 | Fleshner-Barak ............ 514/89 |

FOREIGN PATENT DOCUMENTS

WO WO 01/49295 7/2001
WO WO 01/049295 A1 * 7/2001
WO WO 200149295 A1 * 7/2001

OTHER PUBLICATIONS

Guzzo et al. J. Am. Acad. Dermatol. 1996, vol. 34, pp. 429-433.*
Guzzo et al., J. Am. Acad. Dermatol. 1996, vol. 34, pp. 429-433.*
Price et al, "Osteoprotegerin Inhibits Artery Calcification Induced by Warfarin and by Vitamin D", Arterioscler, Thromb. Vasc. Biol., vol. 21, 2001, p. 1610-1616, Abstract XP-002256098.
Yamaoto, "Method for Preventing Adsorption of Drug", & JP 63057527 A (Toyo Jozo KK). Mar. 12, 1988, Abstract XP002256099.

* cited by examiner

*Primary Examiner*—B. Dell Chism
(74) *Attorney, Agent, or Firm*—Andrus, Sceales, Starke & Sawall, LLP

(57) ABSTRACT

Inhibitors of bone calcium resorption are administered to allow high doses of vitamin D compounds or mimetics to be given with the intent of treating non-calcium related diseases such as cancer, psoriasis, and autoimmune disease without the dangers of calcification of kidney, heart, and aorta. Inhibitors of bone calcium resorption include the bis-phosphonates, OPG (osteoprotegerin) or the soluble RANKL (receptor activator of NF-κB ligand) receptor known as sRANK (soluble RANK which is the protein expressed by the NF-κB gene), and function to block the availability of calcium from bone thereby preventing hypercalcemia and the resulting calcification of soft tissues. Thus, high doses of 1α,25-dihydroxyvitamin $D_3$ (1,25-$(OH)_2D_3$), its analogs, prodrugs, or mimetics can be utilized with minimal risk to a patient. Specifically, alendronate is shown to block the bone calcium mobilization activity of both 1,25-$(OH)_2D_3$ and its very potent analog, 2-methylene -19-nor-(20S)-1α, 25-dihydroxyvitamin $D_3$.

13 Claims, 2 Drawing Sheets

METHOD OF EXTENDING THE DOSE RANGE OF VITAMIN D COMPOUNDS

BACKGROUND AND SUMMARY OF THE INVENTION

Vitamin D intoxication has been known since its discovery in 1922. Of the fat-soluble vitamins, vitamins A and D given at super-physiologic doses will cause toxicity. In the case of vitamin D, the toxicity is the result of elevated blood calcium and blood phosphorus levels that result in calcification primarily of the kidney, heart, aorta and other tissues. Death may result from kidney failure or failure of important organs such as the heart and aorta. It is also known that vitamin D must be metabolized in vivo first in the liver to 25-hydroxyvitamin $D_3$ (25-OH-$D_3$) and then in the kidney to 1,25-dihydroxyvitamin $D_3$ (1,25-$(OH)_2D_3$) before it can carry out its functions. 1,25-$(OH)_2D_3$ then stimulates intestinal calcium and phosphorus absorption, increases the reabsorption of calcium in the kidney, and most importantly, stimulates the mobilization of calcium from bone in a parathyroid hormone dependent process. Thus, an important and unavoidable, until now, activity of the native vitamin D hormone is to mobilize calcium and phosphorus from bone in direct relationship to dose.

It is also known that 1,25-$(OH)_2D_3$ functions through a receptor that dimerizes with the protein, RXR (retinoid X receptor), on responsive elements of target genes to either stimulate or suppresses transcription. The gene products then carry out the functions attributed to 1,25-$(OH)_2D_3$. With the development of receptor knockout mice, and the discovery that Type II vitamin D-dependent rickets is the result of a mutation or mutations in the vitamin D receptor (VDR), it is very clear that most, if not all, actions of vitamin D are mediated through the VDR. This receptor has been found in tissues not previously considered targets of vitamin D action and certainly not considered as playing a role in its functions to mobilize calcium and phosphorus. Such targets are the parathyroid gland, the keratinocytes of skin, the islet cells of the pancreas, and the lymphocytes. Further, Suda and his colleagues (Abe et al, "Differentiation of Mouse Mycloid Leukemia Cells Induced by 1α,25-dihydroxyvitamin $D_3$", Proc. Natl. Acad. Sci., Vol. 78, No. 8, pp. 4990-4994, 1981) have clearly shown that the vitamin D hormone, i.e. 1,25-$(OH)_2D_3$, causes the differentiation of promyelocytes to monocytes, an action not considered to be related to calcium. Because of this differentiation and suppression of growth of cancer tissues in culture, the possibility that vitamin D compounds might be used in a differentiative treatment of cancer has emerged in an enthusiastic fashion. Furthermore, the suppression of autoimmune disease by 1,25-$(OH)_2D_3$ and many of its analogs is also known. The use of topical treatment with vitamin D compounds such as 1,25-$(OH)_2D_3$ and several of its analogs for the disease psoriasis is another well-established fact. However, a main limitation in the realization of these therapies via the administration of vitamin D compounds is that the primary effect of vitamin D compounds is to elevate blood plasma calcium and phosphorus usually at the expense of bone. Thus, if vitamin D compounds are administered in too high a dosage, vitamin D intoxication is a distinct possibility. Attempts have been made to synthesize vitamin D analogs that do not raise blood calcium yet will act in vitro to suppress cancer cells in culture, but so far many of these analogs are non-calcemic because they are rapidly metabolized and rendered inactive. Although that search continues, the present invention provides an alternative route whereby relatively high doses of vitamin D compounds, their analogs, or vitamin D mimetics can be administered without the attendant vitamin D intoxication. Thus, by co-administering agents that block bone calcium mobilization, the mobilization of calcium from bone can be prohibited or prevented or at least minimized, thereby allowing higher and higher doses of vitamin D compounds or mimetics to be used for the treatment of diseases when raising blood calcium is not required. This invention provides that avenue.

The present invention uses a bis-phosphonate, or a calcitonin, or other osteoclastic-mediated bone resorption inhibitor to block bone calcium mobilization and thus prevent the hypercalcemia caused by vitamin D compounds or vitamin D-like mimetics. As a result, high doses of vitamin D compounds can be administered with minimal danger of vitamin D intoxication or hypercalcemia to the patient and with the distinct possibility of suppressing cancer, psoriasis or autoimmune disease. More specifically, the present invention provides a method of administering high doses of a vitamin D compound or a vitamin D mimetic without developing hypercalcemia or resulting in vitamin D intoxication comprising administering to a mammal being treated with a vitamin D compound or vitamin D mimetic an effective amount of a bone calcium resorption inhibitor in an appropriate dosage schedule. A method of treating psoriasis is also provided which comprises administering to a patient with psoriasis an effective amount of a bone calcium resorption inhibitor and an effective amount of a vitamin D compound or vitamin D mimetic in an appropriate dosage schedule. Further, a method of treating a cancer selected from the group consisting of leukemia, colon cancer, breast cancer or prostate cancer comprises administering to a patient with said cancer an effective amount of a bone calcium resorption inhibitor and an effective amount of a vitamin D compound or vitamin D mimetic in an appropriate dosage schedule. Yet another aspect of the present invention is a method of treating an autoimmune disease selected from the group consisting of multiple sclerosis, lupis, inflammatory bowel disease, Type I diabetes, host versus graft reaction, and rejection of organ transplants, comprising administering to a patient with said disease an effective amount of a bone calcium resorption inhibitor and an effective amount of a vitamin D compound or vitamin D mimetic in an appropriate dosage schedule.

The finding that 1,25-$(OH)_2D_3$ causes differentiation of the promyelocytes and suppresses growth of the promyelocytes led several investigators to follow the purpose of this differentiation and has led to the discovery that the vitamin D hormone as well as other agents induce the formation of osteoclasts. The vitamin D hormone appears to be involved not only in the differentiation of monocytes but further in the formation of multinuclear cells and the activation of the multinuclear cells to become active osteoclasts. This is mediated by the vitamin D hormone through its receptor stimulating the production of a protein RANKL which binds to the osteoclast precursors to a RANKL receptor termed RANK located in the membrane surface of osteoclast precursors and mature osteoclasts. It is this signal that then activates both osteoclast development and osteoclast function. A naturally secreted soluble version of RANK called osteoprotegerin (OPG) can block this differentiation or activation process by binding membrane bound or secreted RANKL (See for example PCT Application No. WO 96/26271). Preliminary work has suggested that OPG, or a synthetic recombinant soluble protein comprised of only the extra-cellular domain of RANK (sRANK), will prevent the 1,25-$(OH)_2D_3$-induced increase in serum calcium.

Specifically, this invention utilizes inhibitors of bone calcium mobilization especially the bis-phosphonates, OPG, soluble synthetic RANK, or long-lived chimeric proteins comprised of either OPG or soluble RANK fused to the human Fc (OPG-Fc, sRANK-Fc) to block the availability of calcium from bone thereby preventing hypercalcemia and the resulting calcification of soft tissues. Thus, high doses of $1\alpha,25$-dihydroxyvitamin $D_3$ (1,25-$(OH)_2D_3$), its analogs, prodrugs, or other vitamin D-like compounds (referred to herein as "mimetics") can be utilized with minimal risk of developing hypercalcemia to the patient. Specifically, alendronate is shown to block the bone calcium mobilization activity of both 1,25-$(OH)_2D_3$ and its very potent analog, 2-methylene-19-nor-(20S)-$1\alpha,25$-dihydroxyvitamin $D_3$ (referred to herein as 2MD).

In accordance with the preferred method of the present invention, patients are to be first administered a bone calcium resorption inhibitor such as either the bis-phosphonates, calcitonin, OPG, or sRANK or other similar RANKL binder or inhibitor (OPG-Fc, RANK-Fc) to prevent bone calcium mobilization. Thereafter, the vitamin D analog or compound can be administered in much higher doses than previously thought possible without causing hypercalcemia. Alternately, the bone resorption inhibitor and vitamin D compound can be administered at the same time. This, therefore, will extend the therapeutic dose from 0.5 μg/patient/day in the case of 1,25-$(OH)_2D_3$ to as much as 5 or 10 μg/patient/day when the agents that block bone calcium mobilization are administered. This method will prevent the development of hypercalcemia and will result in achieving concentrations of the vitamin D analogs that can suppress cancer, prevent autoimmune disease, or alleviate psoriasis.

It is expected that the use of this methodology will allow 10-fold or higher increase in dosage level of vitamin D compounds with minimal danger of developing hypercalcemia to the patient.

BRIEF DESCRIPTION OF THE DRAWINGS

The drawings illustrate the best mode presently contemplated of carrying out the invention.

DETAILED DESCRIPTION OF THE INVENTION

Figure 1:
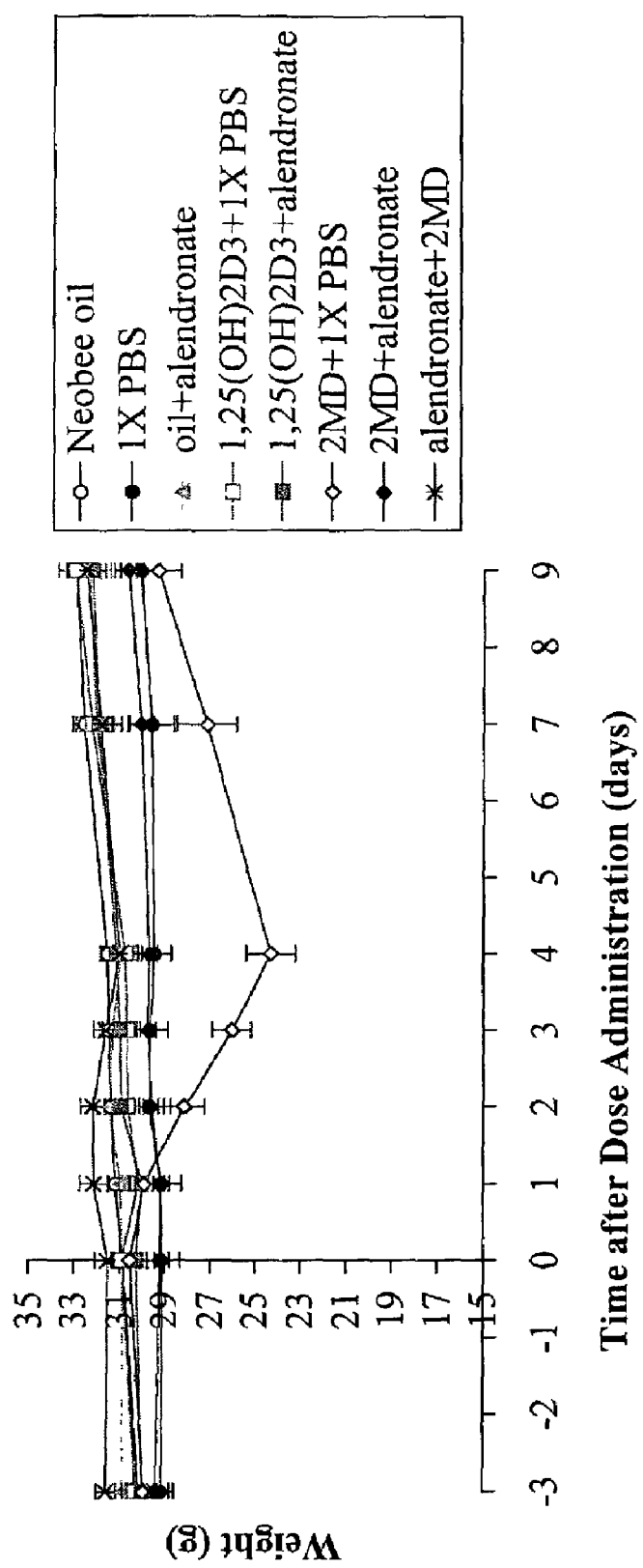
FIG. 1 is a graph of the body weight versus time after dose administration of mice treated in accordance with the present method.
Figure 2:
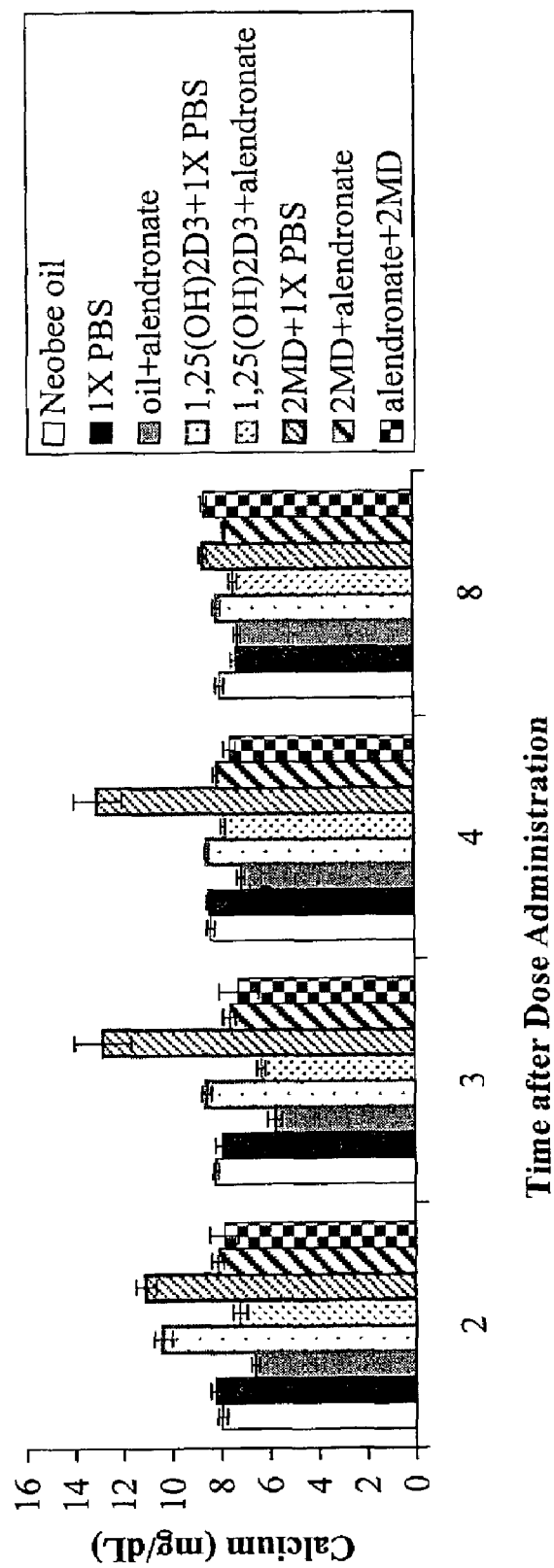
FIG. 2 is a bar graph of serum calcium versus time after dose administration of mice treated in accordance with the present invention.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Preferred hydroxy-protecting groups are those that are base stable but readily removable when desired. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

The terms "hypercalcemia" and "vitamin D toxicity" as used herein refer to a blood serum calcium concentration that is equal to or greater than 2 mg/100 ml of serum. A "toxic dose" of a vitamin D compound is a dose of the vitamin D compound which when administered to a mammal such as a human results in hypercalcemia or vitamin D toxicity.

The term "appropriate dosage schedule" refers to a regimen of administering the vitamin D compound and bone calcium resorption inhibitor to a patient at appropriate doses and at appropriate time intervals in order to effectively treat a targeted disease. As is well known in the pharmaceutical arts, such doses and time intervals may be adjusted according to the disease to be treated, its severity, and the response of the subject being treated.

Vitamin D Compounds

As used herein the term "vitamin D compound" encompasses compounds which control one or more of the various vitamin D-responsive processes in mammals, i.e. intestinal calcium absorption, bone mobilization, bone mineralization, and cell differentiation through activation via the VDR. Thus the vitamin D compounds encompassed by this invention include cholecalciferol and ergocalciferol and their metabolites, as well as the synthetic cholecalciferol and ergocalciferol analogs which express calcemic or cell differentiation activity. The term "vitamin D compound" also includes structurally unrelated vitamin D-like compounds, herein referred to as "vitamin D mimetics," which also activate via the VDR. Without limiting the vitamin D compounds encompassed by the present invention, these synthetic cholecalciferol and ergocalciferol analogs comprise such categories of compounds as the 5,6-trans-cholecalciferols and 5,6-trans-ergocalciferols, the fluorinated cholecalciferols, the side chain homologated cholecalciferols and side chain homologated $\Delta^{22}$-cholecalciferols, the side chain truncated cholecalciferols, the 19-nor cholecalciferols and ergocalciferols, and the 2-substituted cholecalciferols and ergocalciferols.

Structurally, the vitamin D compounds encompassed may be represented by the formula I as follows:

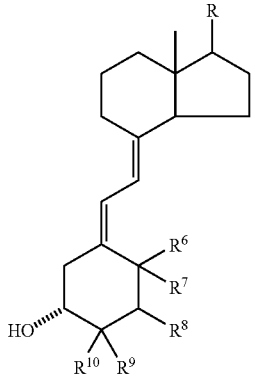

I where $R^6$ and $R^7$ each represent hydrogen or taken together $R^6$ and $R^7$ represent a methylene group, $R^8$ represents hydrogen, hydroxy or a protected hydroxy, $R^9$ and $R^{10}$ may each independently represent hydrogen, alkyl, hydroxyalkyl, or fluoroalkyl, or $R^9$ and $R^{10}$ taken together may represent the group —$(CH_2)_x$— where x is an integer from 2 to 5, the group —OY or =$R^{11}R^{12}$ where $R^{11}$ and $R^{12}$, which may be the same are different, are each selected from hydrogen, alkyl, hydroxyalkyl and fluoroalkyl, or when taken together $R^{11}$ and $R^{12}$ represent the group —$(CH_2)x$— where x is an integer from 2 to 5, and the side chain group R in the above-shown structure, may represent any of the steroid side chain types.

More specifically R can represent a saturated or unsaturated hydrocarbon radical of 1 to 35 carbons, that may be straight-chain, branched or cyclic and that may contain one or more additional substituents, such as hydroxy- or protected-hydroxy groups, fluoro, carbonyl, ester, epoxy, amino or other heteroatomic groups. Preferred side chains of this type are represented by the structure below

where the stereochemical center (corresponding to C-20 in steroid numbering) may have the R or S configuration, (i.e. either the natural configuration about carbon 20 or the 20-epi configuration), and where Z is selected from Y, —OY, —$CH_2$OY, —C≡CY and —CH=CHY, where the double bond may have the cis or trans geometry, and where Y is selected from hydrogen, methyl, —$COR^5$ and a radical of the structure:

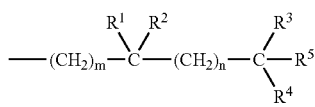

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group, =$CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —$CH(CH_3)$—, —$(CH_2)_m$, —$(CR_1R_2)$— or —$(CH_2)_n$— at positions 20, 22, and 23, respectively, may be replaced by an oxygen or sulfur atom.

The wavy line to the methyl substituent at C-20 indicates that carbon 20 may have either the R or S configuration.

Specific important examples of side chains are the structures represented by formulas (a), b), (c), (d) and (e)

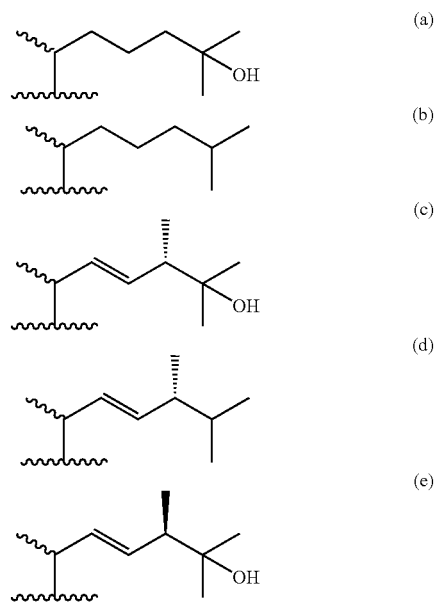

Some specific examples of vitamin D compounds useful herein include vitamin D metabolites or analogs such as vitamin $D_3$, vitamin $D_2$, 1α-hydroxyvitamin $D_3$, 1α-hydroxyvitamin $D_2$, 1α,25-dihydroxyvitamin $D_3$, 1α,25-dihydroxyvitamin $D_2$, 25 hydroxyvitamin $D_3$, 25-hydroxyvitamin $D_2$, 24,24-difluoro-25 hydroxyvitamin $D_3$, 24,24-difluoro-1α,25-dihydroxyvitamin $D_3$, 24-fluoro-25-hydroxyvitamin $D_3$, 24-fluoro-1α,25-dihydroxyvitamin $D_3$, 2β-fluoro-25-hydroxyvitamin $D_3$, 2β-fluoro-1α-hydroxyvitamin $D_3$, 2β-fluoro-1α,25-dihydroxyvitamin $D_3$, 26,26,26,27,27,27-hexafluoro-25-hydroxyvitamin $D_3$, 26,26,26,27,27,27-hexafluoro-1α,25-dihydroxyvitamin $D_3$, 24,25-dihydroxyvitamin $D_3$, 1α,24,25-trihydroxyvitamin $D_3$, 25,26-dihydroxyvitamin $D_3$, 1α,25,26-trihydroxyvitamin $D_3$, 23,25-dihydroxyvitamin $D_3$, 23,25,26-trihydroxyvitamin $D_3$, and the corresponding 1α-hydroxylated forms, 25-hydroxyvitamin $D_3$-26,23-lactone and its 1α-hydroxylated derivative, the side chain nor, dinor, trinor and tetranor-analogs of hydroxyvitamin $D_3$ and of 1α,25-dihydroxyvitamin $D_3$, 1α-hydroxypregnacalciferol, and its homo and dihomo derivatives, 1α,25-dihydroxy-24-epi-vitamin D$_2$, 24-homo-1,25-dihydroxyvitamin D$_3$, 24-dihomo-1,25-dihydroxyvitamin D$_3$, 24-trihomo-1,25-dihydroxyvitamin D$_3$ and the corresponding 26- or 26,27-homo, dihomo or trihomo analogs of 1α,25-dihydroxyvitamin D$_3$ as well as the corresponding 19-nor and 2-substituted compounds of those listed above.

It should be noted in this description that the term "24-homo" refers to the addition of one methylene group and the term "24-dihomo" refers to the addition of two methylene groups at the carbon 24 position in the side chain. Likewise, the term "trihomo" refers to the addition of three methylene groups. Also, the term "26,27-dimethyl" refers to the addition of a methyl group at the carbon 26 and 27 positions so that for example R$^3$ and R$^4$ in formula I are ethyl groups. Likewise, the term "26,27-diethyl" refers to the addition of an ethyl group at the 26 and 27 positions so that R$^3$ and R$^4$ in formula I are propyl groups.

Specific and preferred examples of the vitamin D compounds of structure I when the side chain is unsaturated are:
1α-hydroxy-22-dehydrovitamin D$_3$;
1α,25-dihydroxy-22-dehydrovitamin D$_3$;
25-hydroxy-22-dehydrovitamin D$_3$;
24-homo-1,25-dihydroxy-22-dehydrovitamin D$_3$;
24-dihomo-1,25-dihydroxy-22-dehydrovitamin D$_3$;
24-trihomo-1,25-dihydroxy-22-dehydrovitamin D$_3$;
26,27-dimethyl-24-homo-1,25-dihydroxy-22-dehydrovitamin D$_3$;
26,27-dimethyl-24-dihomo-1,25-dihydroxy-22-dehydrovitamin D$_3$;
26,27-dimethyl-24-trihomo-1,25-dihydroxy-22-dehydrovitamin D$_3$;
26,27-diethyl-24-homo-1,25-dihydroxy-22-dehydrovitamin D$_3$;
26,27-diethyl-24-dihomo-1,25-dihydroxy-22-dehydrovitamin D$_3$;
26,27-diethyl-24-trihomo-1,25-dihydroxy-22-dehydrovitamin D$_3$;
26,27-dipropoyl-24-homo-1,25-dihydroxy-22-dehydrovitamin D$_3$;
26,27-dipropyl-24-dihomo-1,25-dihydroxy-22-dehydrovitamin D$_3$; and
26,27-dipropyl-24-trihomo-1,25-dihydroxy-22-dehydrovitamin D$_3$.

Specific and preferred examples of the vitamin D compounds of structure I when the side chain is saturated are:
1α-hydroxyvitamin D$_3$;
1α,25-dihydroxyvitamin D$_3$;
25-hydroxyvitamin D$_3$;
24-homo-1,25-dihydroxyvitamin D$_3$;
24-dihomo-1,25-dihydroxyvitamin D$_3$;
24-trihomo-1,25-dihydroxyvitamin D$_3$;
26,27-dimethyl-24-homo-1,25-dihydroxyvitamin D$_3$;
26,27-dimethyl-24-dihomo-1,25-dihydroxyvitamin D$_3$;
26,27-dimethyl-24-trihomo-1,25-dihydroxyvitamin D$_3$;
26,27-diethyl-24-homo-1,25-dihydroxyvitamin D$_3$;
26,27-diethyl-24-dihomo-1,25-dihydroxyvitamin D$_3$;
26,27-diethyl-24-trihomo-1,25-dihydroxyvitamin D$_3$;
26,27-dipropyl-24-homo-1,25-dihydroxyvitamin D$_3$;
26,27-dipropyl-24-dihomo-1,25-dihydroxyvitamin D$_3$; and
26,27-dipropyl-24-trihomo-1,25-dihydroxyvitamin D$_3$.

In the above lists of vitamin D compounds, if a particular substituent is attached at the carbon 2 position it should be added to the nomenclature. For example, if an alkyl substituent is attached at the carbon 2 position and a methyl group is the alkyl substituent, the term "2-methyl" should precede each of the named compounds. If an ethyl group is the alkyl substituent, the term "2-ethyl" should precede each of the named compounds, and so on. Also, if an alkylidene substituent is attached at the carbon 2 position and a methylene group is the alkylidene substituent, the term "2-methylene" should proceed each of the named compounds. If an ethylene group is the alkylidene substituent, the term "2-ethylene" should proceed each of the named compounds, and so on. 2-alkyl-19-nor vitamin D compounds are more completely described in U.S. Pat. No. 6,127,559 the disclosure of which is specifically incorporated herein by reference. 2-alkylidene-19-nor vitamin D compounds are more completely described in U.S. Pat. No. 5,843,928 the disclosure of which is specifically incorporated herein by reference. Other vitamin D compounds are disclosed in U.S. Pat. No. 6,369,099 the disclosure of which is specifically incorporated herein by reference. In addition, if the methyl group attached at the carbon 20 position is in its epi or unnatural configuration, the term "20(S)" or "20-epi" should be included in each of the named compounds. The named compounds could also be of the vitamin D$_2$ type having the side chain of formula (c) or (d) above if desired as well as the 19-nor type where the normal methylene group attached at carbon 10 of the A-ring is replaced with two hydrogen atoms. 19-nor vitamin D compounds are more completely described in U.S. Pat. No. 5,587,497 the disclosure of which is specifically incorporated herein by reference.

The preferred vitamin D compounds for use in the methods of the present invention are 1α,25-dihydroxyvitamin D$_3$ and 2-methylene-19-nor-20(S)-1α,25-dihydroxyvitamni D$_3$ (herein referred to as "2MD").

The preparation of the vitamin D compounds, having the basic structure I can be accomplished by a common general method, i.e. the condensation of a bicyclic Windaus-Grundmann type ketone with an allylic phosphine oxide followed by deprotection at C-1 and C-3 in the latter compounds, if desired. This synthesis is well known, and reference is made to U.S. Pat. Nos. 5,843,928 and 5,945,410 for a more detailed illustration of the technique.

Structurally, vitamin D mimetics may be represented by but not limited to the non-secosteroidal VDR ligand reported by Boehm et al. (Chem. Biol. 6:265-275, 1999) and Polek et al. (The Prostate 49:224-233, 2001), or derivatives thereof, the disclosures of each being specifically incorporated herein by reference. Examples of vitamin D mimetics that activate the VDR are those identified by Boehm et al. (Chem. Biol. 6:265-275, 1999) and the bile acid lithocholic acid and several of its derivatives (Makishima et al., Science 296:1313-1316, 2002).

Examples of vitamin D mimetics include, but are not limited to, the following five compounds:

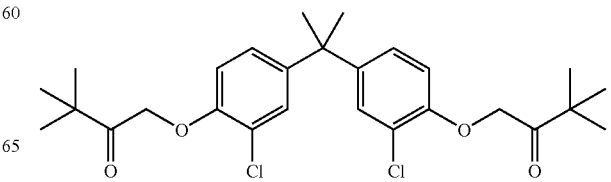

LG190090

-continued

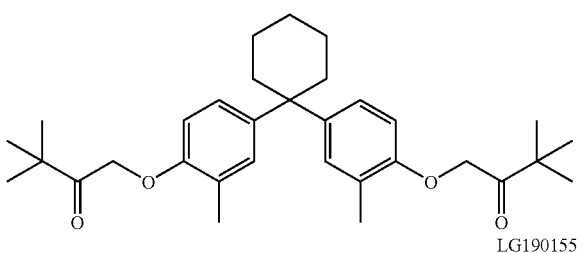
LG190119

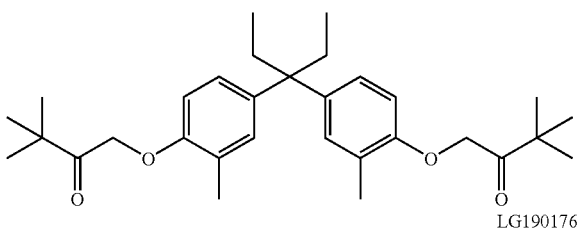
LG190155

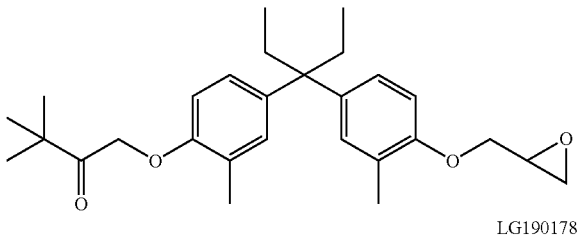
LG190176

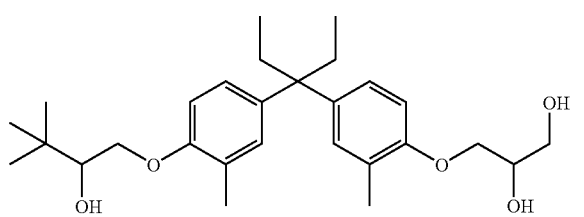
LG190178

Inhibitors of Bone Resorption

As previously stated, inhibitors of bone calcium resorption are administered to prevent the hypercalcemia caused by vitamin D compounds. The term "inhibitor of bone calcium resorption" or "bone calcium resorption inhibitor" encompasses compounds which block or at least substantially block the body's ability to resorb calcium from bone. Such compounds include:

Estrogens,
Androgens,
Cytokines that inhibit bone resorption such as interleukin (IL)-4, IL-12, IL-13, IL-18,
Thiazolidinedione class of activators of peroxisome proliferator activated receptor (PPAR)gamma (e.g. rosglitazone, piaglitazone) (Bendixen et al., Proc. Natl. Acad. Sci. USA 98:2443-2448, 2001),
Calcitonins,
Bisphosphonates (e.g. allendronate, risedronate),
Receptor activator of NFkB (RANK) extracellular domain preparations (Childs et al., J. Bone Miner. Res. 17:192-199, 2002),
RANK mimetics,
Soluble RANK-chimeric proteins (RANK-Fc) (Childs et al., J. Bone Miner. Res. 17:192-199, 2002),
Osteoprotegerin (OPG) (Morony et al., J. Bone Miner. Res. 14:1478-1485, 1999),
OPG chimeric proteins (OPG-Fc) (Morony et al., J. Bone Miner. Res. 14:1478-1485, 1999),
OPG mimetics (Takasaki et al., Nature Biotech 15:1266-1270, 1997),
TNF receptor associated factor 6 (Traf6) decoy peptides (Lomaga et al., Genes & Develop. 13:1015-1024, 1999; Ye et al., Nature 418:443-447, 2002),
Chimeric membrane-permeable Traf6 decoy peptides (Ye et al., Nature 418:443-447, 2002),
Traf6 decoy peptide mimetics,
Inhibitors of src (Wong et al., Mol. Cell 4:1041-1049, 1999),
Inhibitors of the extracellular receptor kinase (ERKs), c-Jun N-terminal kinase (JNKs), stress-activated protein kinase (SAPKs) (p38s) (Darnay et al., J. Biol. Chem. 274:7724-7731, 1999; Matsumoto et al., J. Biol. Chem. 275:31155-31161, 2000),
Peptide/small molecule inhibitors of activator protein-I (AP-1),
Peptide/small molecule inhibitors of c-Fos,
Peptide/small molecule inhibitors of nuclear factor kappa B (NFkB) (Franzoso et al., Genes & Develop. 11:3482-3496, 1997),
Peptide/small molecule inhibitors of inhibitor kinase (IK) beta,
Peptide/small molecule inhibitors of the inhibitory kinase (Ikα, Ikβ, IKKs),
Small molecule antagonists of membrane bound RANK,
Small molecule inhibitors of RANK ligand trimerization or activation,
RGD-containing inhibitors of osteoclast-expressed integrins (Nakamura et al., Endocrinology 139:5182-5193, 1998),
Small molecule mimetics of integrin inhibitors (Nakamura et al., Endocrinology 139:5182-5193, 1998),
Cathespin K inhibitors,
Tartrate resistant acid phosphatase inhibitors, and
Vacuolar ATPase inhibitors.

The above compounds can be used alone or together in various combinations depending upon the desired results.

For treatment purposes, the vitamin D compounds defined by formula I or vitamin D mimetics such as that defined by Boehm et al. (Chem. Biol. 6:265-275, 1999) and Polek et al. (The Prostate 49:224-233, 2001), and the inhibitors of bone calcium resorption may each be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The vitamin D compounds or mimetics and the inhibitors of bone calcium resorption may each be administered orally, topically, parenterally or transdermally. The vitamin D compounds or mimetics and/or the inhibitors of bone calcium resorption are advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.1 μg per day to 100 μg per day of the vitamin D compounds and doses of 7.0 mg per day to 700 mg per day of bone calcium resorption inhibitor are appropriate for treatment purposes, such doses being adjusted according to the disease to be treated, its severity and the response of the subject as is well understood in the art. Typically, a sufficient amount of bone calcium resorption inhibitor is administered so as to provide 0.1 mg/kg to 10 mg/kg of body weight. The vitamin D compounds or mimetics and/or the inhibitors of bone calcium resorption each may be suitably administered independently of each other, or they may be administered simultaneously, in an appropriate dosage schedule, or they may be administered together with graded doses of another vitamin D compound or mimetic and/or inhibitor of bone calcium resorption in situations where different degrees of biological activity is found to be advantageous.

Compositions for use in the above-mentioned treatment of psoriasis, cancer and other malignancies or autoimmune diseases comprise an effective amount of one or more vitamin D compound, as defined by the above formula I, or mimetics, together with one or more inhibitor of bone calcium resorption as defined herein, as the active ingredients, and a suitable pharmaceutical carrier for each. The compositions may be administered substantially simultaneously or the preferred method is for the composition containing the bone calcium resorption inhibitor to be administered first followed by the composition containing the vitamin D compound. It is also contemplated that a single composition could contain both the vitamin D compound or mimetic and the bone calcium resorption inhibitor. An effective amount of each of such compounds for use in accordance with this invention is from about 0.1 µg to 100 µg per gram of composition for vitamin D compounds or mimetics and 7 mg to 700 mg per gram of composition for the bone resorption inhibitors, and may be formulated to be administered topically, transdermally, orally or parenterally.

The compositions may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compositions are advantageously administered in amounts sufficient to result in the desired effect. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

EXAMPLES

Eight-week-old male CD1 mice were obtained from Harlan-Sprague Dawley and fed purified diet 11 containing 0.47% calcium, 0.3% phosphorus, and supplemented with vitamins A,D,E and K as described by Suda et al, "Biological Activity of 25-Hydroxyergocalciferol in Rats," J. Nutrition, Vol. 100, pp. 1049-1052 (1970). Two days after arrival, the rats were then transferred to the same diet 11 but containing 0.02% calcium, 0.3% phosphorus, and the A,D,E and K supplement. Thus, the animals were on a diet essentially devoid of calcium. Two days following shifting of the animals to the low calcium diet, they were given the following doses: 1.7 µg/kg bw and/or 4.5 µg/kg bw 2MD or 500 µg/kg bw 1,25-(OH)2D3. The mice were first divided into 6/group and provided the vitamin D compounds by oral administration at the dose levels shown. Alendronate which was obtained from Sigma was dissolved in phosphate-buffered saline and given interperitoneally in a volume of 100 µL. Serum was collected on days 2, 3, 4 and 8 following treatment. Total serum calcium was measured by Atomic Absorption Spectrometry.

Animals were weighed periodically throughout the study.

Treatment Groups n = 6 animals/group

Group 1 - Neobee oil (4 ml/kg bw)
Group 2 - 1X PBS (100 µl)
Group 3 - alendronate (~1.75 mg/kg bw) + Neobee oil
Group 4 - 2MD (4.5 µg/kg bw in Neobee oil) + 1X PBS
Group 5 - 2MD (4.5 µg/kg bw in Neobee oil) + alendronate (~1.75 mg/kg bw)

-continued n = 6 animals/group

Group 6 - 1,25 (OH)$_2$D$_3$ (500 µg/kg bw in Neobee oil) + 1X PBS
Group 7 - 1,25 (OH)$_2$D$_3$ (500 µg/kg bw in Neobee oil) + alendronate (~1.75 mg/kg bw)
Group 8 - alendronate (1.75 mg/kg in PBS 24 hr prior to 2MID (4 µg/kg bw)

The oil and vitamin D compounds were administered by oral gavage. The alendronate and PBS were administered intraperitoneally in a volume of 100 µl.

Results

As shown in FIG. 1, weights did not change except for the group receiving the 2MD. Thus, a loss of body weight indicative of hypercalcemia and intoxication was clearly evident in mice receiving 2MD. All other groups maintained their weight during the test period. The lower graph demonstrates that 1,25-(OH)$_2$D$_3$ in 2 days caused a significant rise in serum calcium as did the 2MD. After 3 days, 2MD showed further hypercalcemia, while the effect of 1,25-(OH)$_2$D$_3$ had subsided. By day 4, 1,25-(OH)$_2$D$_3$ showed no hypercalcemia, whereas the 2MD still showed hypercalcemic values of 12.5 mg/100 ml. The administration of alendronate clearly blocked the rise in serum calcium caused by either 1,25-(OH)$_2$D$_3$ or 2MD, while alendronate by itself did not change serum calcium concentration. These results demonstrate that the hypercalcemia caused by the mobilization of calcium from bone following treatment with a potent vitamin D analog, 2MD or 1,25-(OH)$_2$D$_3$ itself can be completely prevented by the simultaneous administration of the bis-phosphonate alendronate. Thus, it would be possible to continue treatment of mice with the high level of 2MD safely in the presence of the alendronate and, therefore, can be used to determine efficacy of 2MD against a malignancy or some other disease where calcium is not involved. It is anticipated that calcitonin can be used similarly as can OPG, sRANK, OPG-Fc, or RANK-Fc in preventing the rise in serum calcium at the expense of bone or to prevent hypercalcemia of bone origin.

We claim:

1. A method of treating a disease in a mammal said disease selected from the group consisting of psoriasis, leukemia, colon cancer, breast cancer, prostate cancer, multiple sclerosis, lupus, inflammatory bowel disease, Type I diabetes, host versus graft reaction, and rejection of organ transplants, comprising restricting calcium intake in the mammal's diet, and administering to said mammal orally, parenterally, or transdermally in an appropriate dosage schedule an effective amount of a bone calcium resorption inhibitor and a vitamin D compound, said vitamin D compound administered at a dosage sufficient to treat said disease, said dosage being sufficient to produce hypercalcemia absent the step of administering the bone calcium absorption inhibitor and the step of restricting calcium, said vitamin D compound selected from the group consisting of a compound having the formula

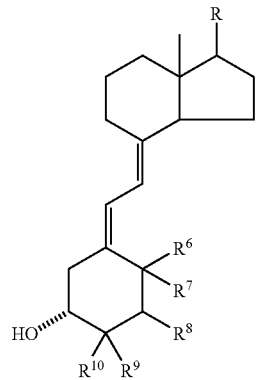

where $R^6$ and $R^7$ each represent hydrogen or taken together $R^6$ and $R^7$ represent a methylene group, $R^8$ represents hydrogen, hydroxy or a protected hydroxy, $R^9$ and $R^{10}$ may each independently represent hydrogen, alkyl, hydroxyalkyl, or fluoroalkyl, or $R^9$ and $R^{10}$ taken together may represent the group —(CH$_2$)$_x$— where x is an integer from 2 to 5, the group —OY or =$R^{11}$ $R^{12}$ where $R^{11}$ and $R^{12}$, which may be the same or different, are each selected from hydrogen, alkyl, hydroxyalkyl and fluoroalkyl, or when taken together $R^{11}$ and $R^{12}$ represent the group —(CH$_2$)x— where x is an integer from 2 to 5 and the group R is represented by the structure

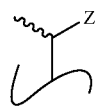

where the stereochemical center at carbon 20 may have the R or S configuration, and where Z is selected from Y, —OY, —CH$_2$OY, —C≡CY and —CH═CHY, where the double bond may have the cis or trans geometry, and where Y is selected from hydrogen, methyl, —COR$^5$ and a radical of the structure:

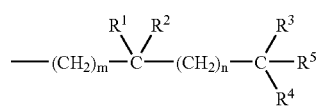

where m and n, independently, represent the integers from 0 to 5, where $R^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group, $=CR^2R^3$, or the group $-(CH_2)_p-$, where p is an integer from 2 to 5, and where $R^3$ and $R^4$, taken together, represent an oxo group, or the group $-(CH_2)_q-$, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups $-CH(CH_3)-$, $-(CH_2)_m-$, $-(CR_1R_2)-$ or $-(CH_2)_n-$ at positions 20, 22, and 23, respectively, may be replaced by an oxygen or sulfur atom.

2. The method of claim 1 wherein the bone calcium resorption inhibitor is administered orally.

3. The method of claim 1 wherein the bone calcium resorption inhibitor is administered parenterally.

4. The method of claim 1 wherein the bone calcium resorption inhibitor is administered transdermally.

5. The method of claim 1 wherein the bone calcium resorption inhibitor is administered in a dosage of from about 0.1 mg/kg to 100 mg/kg of body weight.

6. The method of claim 1 wherein the bone calcium resorption inhibitor is administered before the vitamin D compound.

7. The method of claim 1 wherein the bone calcium resorption inhibitor is administered substantially simultaneously with the vitamin D compound.

8. The method of claim 1 wherein the vitamin D compound is 2-methylene-19-nor-20(S)-1α,25-dihydroxyvitamin $D_3$.

9. The method of claim 1 wherein the vitamin D compound is 1α,25-dihydroxyvitamin $D_3$.

10. The method of claim 1 wherein the vitamin D compound is a vitamin D mimetic selected from any group of compounds that bind to the VDR and activate its transcriptional capability.

11. The method of claim 1 wherein the bone calcium resorption inhibitor is selected from the group consisting of:
Estrogens,
Androgens,
Cytokines that inhibit bone resorption,
Thiazolidinedione class of activators of peroxisome proliferator activated receptor (PPAR)gamma,
Calcitonins,
Bisphosphonates,
Receptor activator of NFkB (RANK) extracellular domain preparations,
RANK mimetics,
Soluble RANK-chimeric proteins (RANK-Fc),
Osteoprotegerin (OPG),
OPG chimeric proteins (OPG-Fc),
OPG mimetics,
TNF receptor associated factor 6 (Traf6) decoy peptides,
Chimeric membrane-permeable Traf6 decoy peptides,
Traf6 decoy peptide,
Inhibitors of src,
Inhibitors of the extracellular receptor kinase (ERKs), c-Jun N-terminal kinase (INKs), or stress-activated protein kinase (SAPKs),
Peptide/small molecule inhibitors of activator protein-I (AP-1),
Peptide/small molecule inhibitors of c-Fos,
Peptide/small molecule inhibitors of nuclear factor kappa B (NFkB),
Peptide/small molecule inhibitors of inhibitor kinase (IK) beta,
Peptide/small molecule inhibitors of the inhibitory kinase (Ikα, Ikβ, IKKs),
Small molecule antagonists of membrane bound RANK,
Small molecule inhibitors of RANK ligand trimerization or activation,
RGD-containing inhibitors of osteoclast-expressed integrins,
Small molecule mimetics of integrin inhibitors,
Cathespin K inhibitors,
Tartrate resistant acid phosphatase inhibitors, and
Vacuolar ATPase inhibitors.

12. The method of claim 1 wherein the bone calcium resorption inhibitor is alendronate.

13. The method of claim 1 wherein the mammal is a human.

\* \* \* \* \*